(12) United States Patent
Taimisto et al.

(10) Patent No.: US 8,043,222 B2
(45) Date of Patent: *Oct. 25, 2011

(54) TRANSDUCER WITH MULTIPLE RESONANT FREQUENCIES FOR AN IMAGING CATHETER

(75) Inventors: Miriam H. Taimisto, San Jose, CA (US); Richard Lardner, San Jose, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 453 days.

This patent is subject to a terminal disclaimer.

(21) Appl. No.: 12/167,802

(22) Filed: Jul. 3, 2008

(65) Prior Publication Data

US 2008/0269615 A1  Oct. 30, 2008

Related U.S. Application Data

(63) Continuation of application No. 10/167,223, filed on Jun. 10, 2002, now Pat. No. 7,396,332.

(51) Int. Cl.
*A61B 8/14* (2006.01)

(52) U.S. Cl. ...................................................... 600/467

(58) Field of Classification Search .......... 600/443–445, 600/454–459, 462–468
See application file for complete search history.

(56) References Cited

U.S. PATENT DOCUMENTS

| | | |
|---|---|---|
| 3,779,234 A | 12/1973 | Eggleton et al. |
| 4,276,491 A | 6/1981 | Daniel et al. |
| 4,697,595 A | 10/1987 | Breyer et al. |
| 4,726,230 A | 2/1988 | Yoshikawa et al. |
| 4,860,758 A | 8/1989 | Yanagawa et al. |
| 4,870,972 A | 10/1989 | Maerfeld et al. |
| 4,951,677 A | 8/1990 | Crowley et al. |
| 4,963,782 A | 10/1990 | Bui et al. |
| 5,060,653 A | 10/1991 | Dias |
| 5,163,436 A | 11/1992 | Saitoh et al. |
| 5,269,307 A | 12/1993 | Fife et al. |
| 5,284,148 A | 2/1994 | Dias et al. |

(Continued)

FOREIGN PATENT DOCUMENTS

JP  03-155840  7/1991

(Continued)

OTHER PUBLICATIONS

Database Biosis 'Online! Biosciences Information Services, Philadelphia, PA, US; 1996 Montauban Van Swijndregt Alexander D. et al: "An in vitro evaluation of the line pattern of the near and far walls of carotid arteries using B-mode ultrasound." Database accession No. PREV199799326895 XP002251664 abstract & Ultrasound in Medicine and Biology, vol. 22, No. 8, 1996, pp. 1007-1015, ISSN 0301-5629.

(Continued)

*Primary Examiner* — Michael T Rozanski
(74) *Attorney, Agent, or Firm* — Frommer Lawrence & Haug LLP; Bruce E. Black

(57) ABSTRACT

A single transducer element that is capable of oscillation at a plurality of natural resonant frequencies may be used in an ultrasonic imaging catheter assembly including a catheter body configured to be inserted and guided through the vascular system of a living being, a lumen and a rotatable imaging core adapted to pass through the lumen, the imaging core including a flexible drive-shaft. Because the transducer element is capable of oscillation at a plurality of natural resonant frequencies, a user can switch from one frequency to another in order to improve the depth of field or resolution without having to switch out the catheter or imaging core.

20 Claims, 1 Drawing Sheet

U.S. PATENT DOCUMENTS

| | | | |
|---|---|---|---|
| 5,351,693 A | 10/1994 | Taimisto et al. |
| 5,360,007 A | 11/1994 | Shinomura et al. |
| 5,410,205 A | 4/1995 | Gururaja |
| 5,423,319 A | 6/1995 | Seyed-Bolorforosh |
| 5,438,554 A | 8/1995 | Seyed-Bolorforosh et al. |
| 5,460,595 A | 10/1995 | Hall et al. |
| 5,464,016 A | 11/1995 | Nicholas et al. |
| 5,825,117 A | 10/1998 | Ossmann et al. |
| 5,938,612 A | 8/1999 | Kline-Schoder et al. |
| 6,004,269 A | 12/1999 | Crowley et al. |
| 6,074,349 A | 6/2000 | Crowley |
| 6,233,476 B1 | 5/2001 | Strommer et al. |
| 6,361,500 B1 | 3/2002 | Masters |
| 6,457,365 B1 | 10/2002 | Stephens et al. |
| 6,558,331 B1 | 5/2003 | Davidsen et al. |
| 6,719,700 B1 | 4/2004 | Willis |
| 6,780,157 B2 | 8/2004 | Stephens et al. |
| 6,958,040 B2 | 10/2005 | Oliver et al. |

FOREIGN PATENT DOCUMENTS

| | | |
|---|---|---|
| JP | 05042148 | 2/1993 |
| JP | 05056977 | 3/1993 |
| JP | 05285140 | 11/1993 |
| JP | 06022963 | 2/1994 |
| JP | 06261395 | 9/1994 |
| JP | 09000522 | 1/1997 |
| JP | 09117452 | 5/1997 |
| JP | 09215094 | 8/1997 |
| JP | 10277038 A | 10/1998 |
| WO | WO-02/069806 | 9/2002 |

OTHER PUBLICATIONS

Database Inspec 'Online! Institute of Electrical Engineers, Stevenage, GB; Goodings G A W et al: Transducer frequency considerations in intraoperative US of the spine: Database accession No. 2765019 XP002251665 abstract & Radiology, Jul. 1986, USA vol. 160, No. 1, pp. 272-273, ISSN 003-8419.

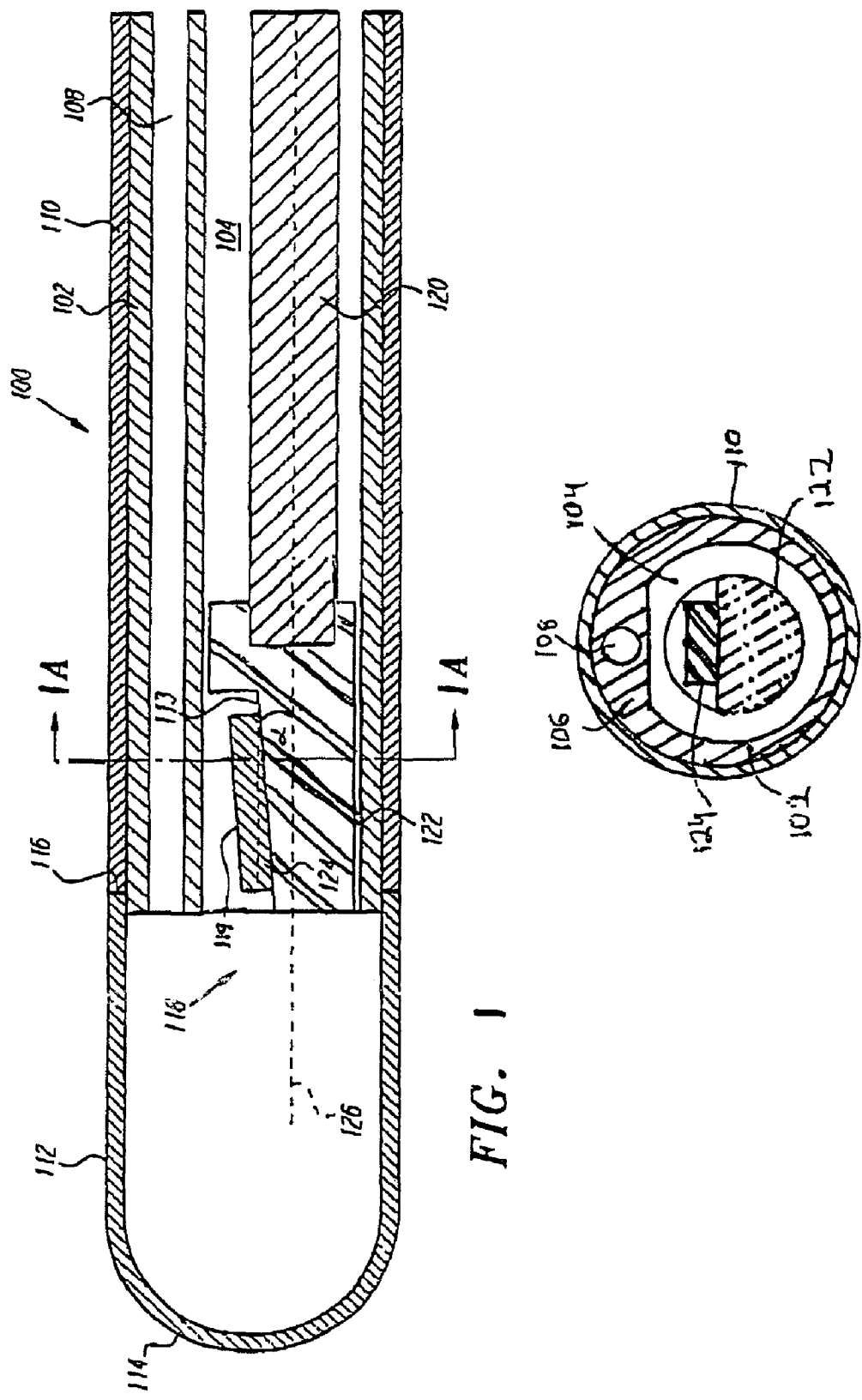

TRANSDUCER WITH MULTIPLE RESONANT FREQUENCIES FOR AN IMAGING CATHETER

FIELD OF THE INVENTION

The present invention relates generally to the field of medical ultrasonic catheters, and in particular, to a transducer element having multiple resonant frequencies for use in ultrasonic imaging medical catheters.

BACKGROUND OF THE INVENTION

In recent years, the use of ultrasound systems for medical diagnostics has continued to grow. Ultrasonic systems are used in a vast array of medical fields and diagnostic areas. As the desire to use ultrasonic imaging systems has grown, so has the level of sophistication of those systems.

To assist physicians and staff in performing diagnostic and therapeutic procedures, a number of ultrasonic imaging systems have been designed for use with catheters. In general, these systems comprise a single transducer element, frequently made of piezoelectric material, attached to the distal portion of an imaging catheter. The imaging catheter is inserted into the patient so that the transducer is positioned to image a desired region of the patient's anatomy.

Such catheters typically operate by sending an electrical signal or excitation pulse to the transducer. The transducer then converts the electrical energy into mechanical energy, which propagates into a patient's surrounding body tissues as ultrasonic waves. The frequency of the emitted ultrasonic waves are a function of the resonant frequency of the transducer element and the frequency content of the excitation pulse. The ultrasonic waves are reflected back to the transducer as reflected signals or echoes, which the transducer converts into an electrical signal, which is used to produce an image of the patient's anatomy.

By operating with a transducer having only one resonant frequency, however, the focusing capability of the imaging catheters is limited. The frequency of emitted sound waves is a function of the resonant frequency and bandwidth of the transducer element and the frequency content of the excitation pulse, and can only be altered by varying the excitation pulse frequency. As a result, the ability of the single resonant frequency transducer element to be focused at different depths into the surrounding tissue is limited.

Other catheter systems attempt to solve the focusing problem by switching out the catheter or imaging core during operation so that the replacement catheter would contain a transducer element with a different frequency. However, this method of catheter replacement is very time-consuming which necessarily makes the imaging procedure longer than is necessary.

Therefore, there exists a present need to provide a multiple resonant frequency transducer for an imaging catheter system, which is capable of providing high quality ultrasound images at different depths without having to switch out the catheter or the imaging core.

SUMMARY OF THE INVENTION

A first, separate aspect of the invention involves an ultrasonic imaging catheter assembly including a catheter body configured to be inserted and guided through the vascular system of a living being, the catheter body having a distal end, a proximal end, and a lumen extending through its longitudinal axis. The ultrasonic imaging catheter assembly further includes a rotatable imaging core adapted to pass through the lumen, the imaging core including a flexible drive-shaft and a single transducer element that is capable of oscillation at a plurality of natural resonant frequencies.

A second, separate aspect of the invention involves an ultrasonic imaging catheter assembly including a transducer having a plurality of natural resonant frequencies including a lower resonant frequency and a higher resonant frequency. During use in the vascular system of a living body, the transducer can be switched between the lower resonant frequency and the higher resonant frequency, wherein the transducer element is to be oscillated at the lower resonant frequency to optimize depth of penetration and wherein the transducer element is to be oscillated at the higher resonant frequency to optimize resolution. Switching between resonant frequencies is accomplished using, for example, an external instrument console and, consequently, does not require removal of the catheter body or imaging core from the vascular system of the living body.

A third, separate aspect of the invention involves an ultrasonic imaging catheter assembly including a transducer having a plurality of natural resonant frequencies including a lower resonant frequency, a middle frequency and a higher resonant frequency, wherein for example, the lower frequency is about 7.5 MHz, the middle frequency is about 10 MHz and the higher frequency is about 30 MHz. During use within the vascular system of a living being, the different frequencies can be used for different purposes. For instance, the lower frequency may be adapted for imaging within arteries, the middle frequency may be adapted for guiding the catheter into place and the higher frequency may be adapted for imaging within the heart.

A fourth, separate aspect of the invention involves an ultrasonic imaging catheter assembly including a generally disk-shaped cylindrical transducer formed from piezoelectric ceramic materials, piezocomposite materials, piezoelectric plastics, barium titanates, lead zirconate titanates, lead metaniobates, or polyvinylidenefluorides. The transducer is attached to the drive-shaft by a transducer housing, wherein the transducer may be mounted in a cut-away portion of the transducer housing such that it slopes at an angle with respect to the central axis of the drive-shaft to reduce internal reflections inside the catheter.

The invention may include any one of these separate aspects individually, or any combination of these separate aspects.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the invention, in which similar elements are referred to by common reference numerals.

FIG. 1 is a cut-away partial side view of an ultrasound catheter assembly.

FIG. 1A is a cross-sectional view of the ultrasound catheter assembly of FIG. 1 taken along line 1A-1A.

DESCRIPTION OF THE PREFERRED EMBODIMENT

The improved transducer element having multiple resonant frequencies may be used, for example, in an ultrasound imaging system. Mechanical scanning ultrasound imaging catheter systems typically employ a single transducer mounted inside a rotating housing. In one example, the transducer transmits and receives ultrasonic waves while the transducer housing rotates about a fixed axis in an acoustic window located at a distal tip of the catheter. The rotational motion of the transducer housing is accomplished by a flexible drive-shaft that extends through an axially disposed lumen of the catheter, wherein the drive-shaft has one end connected to the transducer housing. Once the distal end of the catheter is positioned, for example, in a patient's vascular system, a cross-sectional image of the tissue surrounding the distal catheter tip is produced by using imaging and control circuitry that are electrically coupled to the transducer via an electrical conductor extending through the drive shaft.

FIGS. 1 and 1A illustrate an example embodiment of a flexible ultrasound catheter 100. Ultrasound catheter 100 is adapted to be positioned within the vascular system by standard, well-known catheter procedures by guiding the flexible catheter 100 through various blood vessels along a circuitous path, beginning, for example, by percutaneous introduction through a perforation of the femoral artery.

The catheter includes an elongate tubular member 102, which forms an axially disposed lumen 104. The inner dimensions of lumen 104 are sufficient to allow an imaging core 118 to be slidably disposed therein. The imaging core includes a flexible drive-shaft 120 connected to a transducer housing 122 having a generally disk-shaped transducer 124 mounted therein. The imaging core 118 is capable of translation along its central axis. In addition, imaging core 118 is capable of rotation about its central axis at speeds in excess of 1800 rpm. Further disclosure concerning rotatable, motor-driven imaging cores can be found in U.S. Pat. No. 6,004,269, which is incorporated herein by reference.

A dome-shaped acoustic imaging window 112 is attached to a distal end of the elongate tubular element 102, thereby forming an enclosed tip of the catheter 100. Alternatively, the shape of the acoustic imaging window 112, the transducer 124, or any other component may be virtually any shape or combination of shapes. A cover tube 110 formed of a suitable material, such as a heat shrinkable nylon, urethane, polyethylene or other plastic, is disposed around tubular element 102, wherein cover tube 110 provides both structural integrity to the catheter 100, as well as a smooth outer surface for ease in axial movement in a patient's body passage with minimal friction.

Preferably, the acoustic imaging window 112 has its proximal end open and its distal end rounded and is attached to a distal outer circumferential portion of the tubular element 102 to form an enclosed catheter tip 114, with respective ends of the cover tube 110 and acoustic imaging window 112 bonded together at a common joint 116. The outer diameter of the proximal end of window 112 is substantially equal to that of the installed cover tube 110, so that a smooth outer surface is provided at joint 116. As best seen in FIG. 1, optional upper portion 106 of the elongate tubular member 102 forms a smaller lumen 108, which can be used for other catheter functions such as, by way of non-limiting examples, housing pullwires, drug delivery, balloon angioplasty, laser ablation, or for housing a stiffening member to help prevent the collapsing of the catheter 100. Of course, the catheter may have any number of lumens of any configuration. The catheter could have a balloon or a plurality of balloons, if desired. The catheter could also have more than one window, wires embedded in the catheter walls, multiple transducers, or other features known in the field. For example, the catheter could use another transducer in addition to the multiple resonant frequency transducer. Optionally, the catheter could even use a plurality of multiple resonant frequency transducers.

With further reference to the particular example shown in FIG. 1, the transducer housing 122 has a longitudinally disposed cut-away portion 113, which slopes at a slight angle, alpha, with respect to the central axis 126 of drive-shaft 120. The transducer 124 is mounted in the cut-away portion 113 of the transducer housing 122 such that its active surface 119 also slopes at angle alpha with respect to central axis 126 of drive-shaft 120. This tilting of transducer 124 helps to minimize internal reflections inside of catheter tip 114.

Although the preferred transducer 124 of the present invention is disk-shaped, it may, alternatively, be any other shape. In use, it converts electrical energy pulses into mechanical energy, which propagates out from the face of the transducer 124 in the form of ultrasonic waves. The frequencies of these ultrasonic waves are dependent upon the excitation frequencies and the natural resonant frequencies of the transducer 124. The natural resonant frequencies of the transducer 124 are a product of the shape and thickness of the transducer 123 and the transducer material.

Transducer 124 is formed in a known manner from materials capable of transforming pressure distortions on its surface into electrical voltages and vice versa. Such materials include, but are not limited to piezoelectric ceramic materials, piezocomposite materials, piezoelectric plastics, barium titanates, lead zirconate titanates, lead metaniobates and polyvinylidenefluorides.

As discussed above, the frequency at which the transducer 124 emits ultrasonic waves is a function of the resonant frequencies of the transducer 124 and the frequency of the excitation pulse sent to the transducer 124. When the ultrasonic waves impinge on an object, the ultrasonic waves are reflected back to the transducer 124, which converts the mechanical energy back into an electrical signal. The electrical signal from the transducer 124 is transmitted from the distal end of the catheter 100 to the catheter system's imaging equipment by a transmission line.

By using an imaging catheter 100 with a transducer 124 having multiple resonant frequencies, a user is capable of producing images having varying characteristics depending upon which frequency is utilized. Two important imaging characteristics are depth of field and resolution. Depth of field permits greater penetration during operation, which can be useful for imaging the in the heart, for example. High resolution is important for close-up imaging within a vessel such as a coronary artery. However, good depth of field comes at the expense of lower resolution and vice versa. Preferably, the improved transducer 124 is capable of operating at low, middle and high resonant frequencies in order to take advantage of the differing imaging characteristics of each frequency.

As an example, the multiple resonant frequency catheter 100 of the present invention can be configured to have three resonant frequencies at 30 MHz, 10 MHz and 7.5 MHz. In a single procedure, all three frequencies can be employed by a user. As an example, suppose an imaging procedure entails first imaging a coronary artery, then guiding the catheter 100 into the right atrium and then imaging the left atrium. To image the coronary artery, the transducer 124 should be operated at the 30 MHz frequency since the higher frequency yields good close-up resolution.

After imaging the coronary artery, the catheter must be guided into the right atrium. Since guiding the catheter into place requires both depth of field and resolution, the middle range frequency of 10 MHz is preferred for this maneuver. Upon guiding the catheter into place in the right atrium, the left atrium is to be imaged. Imaging the atrium at a distance will require considerable depth of field and the lower 7.5 MHz resonant frequency will, therefore, be preferable at this stage. In this manner, all three resonant frequencies can be employed in a typical imaging procedure. However, this procedure is merely one example of a myriad of imaging procedures that require a transducer to operate at multiple frequencies.

Because the multiple resonant frequency transducer 124 is capable of oscillation at three resonant frequencies, the catheter and/or imaging core does not have to be switched out during operation. Switching catheters out is a timely procedure, which necessarily makes the imaging procedure longer than is necessary. Instead, a catheter can use a single transducer 124 having multiple resonant frequencies, without having to sacrifice depth of field or resolution. Switching between resonant frequencies may be accomplished, for example, using an external instrument console. Any number of typical instrument console expedients can be used to accomplish this task including a button, dial, switch, voice command, mouse, track ball, or pointing device.

Any one or more of the features depicted in FIGS. 1 and 1A, or described in the accompanying text, may be interchanged with that of another figure to form still other embodiments.

While preferred embodiments and methods have been shown and described, it will be apparent to one of ordinary skill in the art that numerous alterations may be made without departing from the spirit or scope of the invention. Therefore, the invention is not limited except in accordance with the following claims.

What is claimed is:

1. An ultrasonic imaging system comprising;
   an external instrument console; and
   a catheter coupled to the external instrument console, the catheter comprising
   a catheter body configured to be inserted and guided through a blood vessel of a vascular system of a living being, the catheter body having a distal end, a proximal end, and a lumen extending through its longitudinal axis; and
   a rotatable imaging core adapted to pass through the lumen, the imaging core including a flexible driveshaft and a discrete transducer element;
   wherein the discrete transducer element is capable of oscillation at a plurality of natural resonant frequencies and is configurable to be switchable between the plurality of natural frequencies using the external instrument console, and wherein each natural resonant frequency provides a unique depth of field and resolution in an image generated at the respective frequency.

2. The ultrasonic imaging system of claim 1, wherein the external instrument console comprises a switching mechanism for switching between the plurality of natural frequencies of the discrete transducer element.

3. The ultrasonic imaging system of claim 2, wherein the switching element mechanism comprises at least one button, dial, or switch.

4. The ultrasonic imaging system of claim 2, wherein the switching element comprises at least one mouse, track ball, or other pointing device.

5. The ultrasonic imaging system of claim 1, wherein the catheter comprises a plurality of the discrete transducer elements.

6. The ultrasonic imaging system of claim 1, wherein the catheter further comprises a second lumen.

7. The ultrasonic imaging system of claim 6, wherein the catheter further comprise a steering pullwire disposed in the second lumen.

8. A method of imaging within a vascular system of a living being, the method comprising:
   inserting a catheter into the vascular system, the catheter comprising a distal end, a proximal end, a lumen extending along a longitudinal axis of the catheter, and a rotatable imaging core disposed in the lumen, wherein the rotatable imaging core comprises a flexible drive-shaft and a discrete transducer element, wherein the discrete transducer element is configured and arranged for oscillation at a plurality of natural resonant frequencies, and wherein each natural resonant frequency provides a unique depth of field and resolution in an image generated at the respective frequency;
   selecting a first one of the natural frequencies of the discrete transducer element;
   generating ultrasound waves at the first one of the natural frequencies using the discrete transducer element; and
   receiving reflected ultrasound waves at the discrete transducer element.

9. The method of claim 8, further comprising generating an ultrasound image from the received ultrasound waves.

10. The method of claim 8, further comprising selecting a second one of the natural frequencies of the discrete transducer element and generating ultrasound waves at the second one of the natural frequencies using the discrete transducer element.

11. The method of claim 10, further comprising moving the discrete transducer element from a first location to a second location within the living being after generating ultrasound waves at the first one of the natural frequencies and prior to generating ultrasound waves at the second one of the natural frequencies.

12. The method of claim 11, wherein a one of the first and second locations is within a blood vessel of the vascular system and another of the first and second locations is within a heart.

13. The method of claim 12, wherein the plurality of natural frequencies comprises a high frequency and a low frequency.

14. The method of claim 13, wherein the high frequency is selected when the discrete transducer element is located within the blood vessel.

15. The method of claim 14, wherein the low frequency is selected when the discrete transducer element is located within the heart.

16. The method of claim 11, further comprising selecting a third one of the natural frequencies of the discrete transducer element and generating ultrasound waves at the third one of the natural frequencies using the discrete transducer element while disposed at the second location.

17. The method of claim 10, further comprising selecting a third one of the natural frequencies of the discrete transducer element and generating ultrasound waves at the third one of the natural frequencies using the discrete transducer element.

18. The method of claim 17, further comprising moving the discrete transducer element to a third location within the living being after generating ultrasound waves at the second one of the natural frequencies and prior to generating ultrasound waves at the third one of the natural frequencies.

19. The method of claim 18, further comprising moving the discrete transducer element from a first location to a second location within the living being after generating ultrasound waves at the first one of the natural frequencies and prior to generating ultrasound waves at the second one of the natural frequencies.

20. The method of claim 19, wherein a one of the first, second, and third locations is within a blood vessel of the vascular system and another of the first, second, and third locations is within a heart.

* * * * *